(12) United States Patent
Wu et al.

(10) Patent No.: US 12,383,901 B2
(45) Date of Patent: Aug. 12, 2025

(54) DIGITAL PCR SYSTEM AND DIGITAL PCR DROPLET FORMATION METHOD

(71) Applicant: SHANGHAI AUREFLUIDICS TECHNOLOGY CO., LTD., Shanghai (CN)

(72) Inventors: Xuanye Wu, Shanghai (CN); Yimin Guan, Shanghai (CN)

(73) Assignee: SHANGHAI AUREFLUIDICS TECHNOLOGY CO., LTD., Shanghai (CN)

(*) Notice: Subject to any disclaimer, the term of this patent is extended or adjusted under 35 U.S.C. 154(b) by 1068 days.

(21) Appl. No.: 17/044,509

(22) PCT Filed: Nov. 23, 2018

(86) PCT No.: PCT/CN2018/117311
§ 371 (c)(1),
(2) Date: Oct. 1, 2020

(87) PCT Pub. No.: WO2020/034483
PCT Pub. Date: Feb. 20, 2020

(65) Prior Publication Data
US 2021/0362158 A1    Nov. 25, 2021

(30) Foreign Application Priority Data

Aug. 13, 2018  (CN) .......................... 201810916060.6

(51) Int. Cl.
*B01L 3/00* (2006.01)
*B01L 7/00* (2006.01)

(52) U.S. Cl.
CPC ... *B01L 3/502784* (2013.01); *B01L 3/502715* (2013.01); *B01L 7/525* (2013.01);
(Continued)

(58) Field of Classification Search
CPC ......... B01L 3/502784; B01L 3/502715; B01L 7/525; B01L 2200/10; B01L 2300/048;
(Continued)

(56) References Cited

U.S. PATENT DOCUMENTS 6,633,785 B1 * 10/2003 Kasahara .................. B01L 7/52
435/286.1
2006/0144972 A1 * 7/2006 Kelly ...................... F23D 11/32
239/690

(Continued)

FOREIGN PATENT DOCUMENTS

CN       104046556 A2    9/2014
CN       104487592 A     4/2015
(Continued)

OTHER PUBLICATIONS

Fan, Yiqiang et al., Recent Development of Droplet Microfluidics in Digital Polymerase Chain Reaction, Chinese Journal of Analytical Chemistry, 2016, 9 Pages.

*Primary Examiner* — Jill A Warden
*Assistant Examiner* — Jacqueline Brazin
(74) *Attorney, Agent, or Firm* — Metis IP LLC

(57) ABSTRACT

A digital PCR system has at least one droplet forming assembly and a droplet spraying hole assembly. The droplet forming assembly has at least one droplet collecting tank; the droplet spraying hole assembly is connected below the droplet forming assembly. The droplet spraying hole assembly has a plurality of droplet spraying holes in communication with the droplet collecting tank. Vaporization parts are provided in the droplet spraying holes and used for vaporizing digital PCR solution liquid layers in the droplet spraying holes and quickly pushing the vaporized digital PCR solution liquid layers into droplet forming oil in the droplet collecting tank to form digital PCR droplets.

19 Claims, 13 Drawing Sheets

(52) U.S. Cl.
CPC ..... *B01L 2200/10* (2013.01); *B01L 2300/048* (2013.01); *B01L 2400/0487* (2013.01)

(58) Field of Classification Search
CPC ..... B01L 2400/0487; B01L 2300/0838; B01L 2400/0442; C12M 1/00; C12M 1/36; C12M 1/38; C12Q 1/6851
USPC ...................................................... 435/287.2
See application file for complete search history.

(56) References Cited

U.S. PATENT DOCUMENTS

| | | | |
|---|---|---|---|
| 2007/0161135 A1* | 7/2007 | Keller | B41J 3/407 |
| | | | 438/22 |
| 2008/0056948 A1* | 3/2008 | Dale | B01L 3/502715 |
| | | | 422/68.1 |
| 2011/0237463 A1* | 9/2011 | Araki | B01J 19/0046 |
| | | | 506/30 |
| 2011/0312856 A1* | 12/2011 | Silverbrook | F16K 99/003 |
| | | | 506/40 |
| 2016/0310948 A1* | 10/2016 | Nowakowski | B01L 3/502723 |
| 2020/0001301 A1 | 1/2020 | Shi et al. | |

FOREIGN PATENT DOCUMENTS

| | | |
|---|---|---|
| CN | 104611223 A | 5/2015 |
| CN | 106520524 A | 3/2017 |
| CN | 106754341 A | 5/2017 |
| CN | 106824313 A | 6/2017 |
| CN | 106834115 A | 6/2017 |
| CN | 108265005 A | 7/2018 |
| WO | 2017004250 A1 | 1/2017 |
| WO | 2017209906 A1 | 12/2017 |

* cited by examiner

DIGITAL PCR SYSTEM AND DIGITAL PCR DROPLET FORMATION METHOD

TECHNICAL FIELD

The present invention belongs to the field of biomedicine, in particular to the field of disease diagnostics, and relates to a digital PCR system and a method for generating digital PCR droplets.

BACKGROUND ART

Polymerase chain reaction (PCR) has been proposed for 20 years, during which PCR has developed into a key and conventional technique in the area of molecular biology, greatly promoting the development of various areas of life sciences. In particular, in the late 1990s, ABI in the United States not only introduced the real-time fluorescent quantitative PCR (real time PCR, qPCR) technique and related products, but also developed PCR from a technique for in-vitro synthesis and qualitative/semi-quantitative detection into a highly sensitive, highly specific and accurate quantitative technique for gene analysis.

Despite rapid development more than 10 years, qPCR technique has been used for diagnosis of all diseases except injuries and nutrient deficiencies. However, the PCR amplification efficiency is affected by many factors during amplification. It cannot ensure the same amplification efficiency during reaction, or between the actual samples and the standard samples, and among various samples. Thus, the cycle threshold (CT) which is the basis of quantitative analysis, is not constant. Therefore, the quantification of qPCR is only "relative quantification", and its accuracy and reproducibility still cannot meet the requirements of quantitative analysis in molecular biology.

At the end of the $20^{th}$ century, Vogelstein et al. proposed the concept of a digital PCR (dPCR), which involved distributing a sample into tens to tens of thousands of parts to different reaction units. Each unit contained one or a few copies of a target molecule (Template DNA). In each reaction unit, the target molecule was amplified by PCR, and the fluorescence signal of each reaction unit was statistically analyzed after completion of the amplification reaction. Unlike qPCR, digital PCR did not depend on CT values, so it was not affected by amplification efficiency. After completion of the amplification reaction, the average concentration (content) in each reaction unit was calculated by directly counting or using the Poisson distribution equation, and the error could be controlled within 5%. Digital PCR enabled the absolute quantitative analysis without the need for standard samples and curves.

Digital PCR (also known as a single molecule PCR) generally comprises two parts, i.e. PCR amplification and fluorescence signal analysis. At the PCR amplification stage, unlike traditional techniques, samples in digital PCR are generally required to be diluted to the level of single molecules and evenly distributed into tens to tens of thousands of units for reaction. Unlike qPCR, which measures real-time fluorescence at each cycle, the digital PCR technique collects the fluorescence signal in each reaction unit after amplification. Finally, the original concentrations or contents of the samples are calculated by directly counting or using the Poisson distribution equation.

Since digital PCR is a technique for absolute quantification of nucleic acid molecules, and compared with qPCR, it can directly count the number of DNA molecules, which is to absolutely quantify starting samples, digital PCR is especially suitable for application fields where it cannot be well distinguished from CT values, such as copy number variation, mutation detection, relative gene expression studies (e.g., allelic imbalance gene expression), validating second-generation sequencing, miRNA expression analysis, single-cell gene expression analysis etc.

At present, there are three main types of digital PCR techniques on the market. One is to generate droplets by shearing an aqueous PCR solution with flowing oil in a specific apparatus, and then complete PCR and detection in other two apparatuses; another one is to distribute a PCR solution onto a hollow silicon wafer, then perform PCR in a specific apparatus and detect in another apparatus; the last one is to generate droplets by injecting a liquid into a chamber through a narrow channel in one apparatus and complete PCR, and then complete detection in another apparatus. However, the current three methods have limitations on the flux or the rate of droplet generation. Furthermore, the above three techniques rely on multiple large apparatuses without exception. This not only increases the purchase cost of apparatuses and limits the widespread use of digital PCR, but also increases the complexity of experimental operations.

Therefore, it has become an important technical problem to be solved urgently by those skilled in the art: how to provide a technique for high-speed digital PCR droplet generation at a rate of more than 1000 droplets per second, an in-situ PCR technique for integrating droplet generation with PCR temperature control and detection instruments, and a method for an efficient utilization rate of digital PCR oil.

SUMMARY OF THE DISCLOSURE

In view of the above-mentioned disadvantages of the prior art, an object of the present invention is to provide a digital PCR system and a method for generating digital PCR droplets to solve the problems of slow droplet generation rate, small flux, complicated operation and low utilization rate of PCR oil in the prior art.

To achieve the above object and other related objects, the present invention provides a digital PCR system, comprising:

at least one droplet generation component, comprising at least one droplet collection groove;

a droplet nozzle member, connected below the droplet generation component, comprising a plurality of droplet nozzles; the droplet nozzles have openings on the upper surface of the droplet nozzle member, and extend toward, but not through, the lower surface of the droplet nozzle member, the droplet nozzles are in communication with the droplet collection groove, and vaporizing parts being provided in the droplet nozzles for vaporizing liquid layers of a digital PCR solution in the droplet nozzles, and rapidly pushing the vapor into droplet generating oil in the droplet collection groove to generate digital PCR droplets.

Optionally, the droplet nozzle member comprises thermal bubble print chips.

Optionally, the vaporizing parts are arranged on lower surfaces or sidewall of the droplet nozzles.

Optionally, the shape of the opening of each of the droplet nozzles comprises any one selected from the group consisting of round, ellipse and polygon.

Optionally, the vaporizing parts comprise heating elements for vaporizing the liquid layers of the digital PCR solution by heating.

Optionally, the heating elements comprise at least one metal layer.

Optionally, a through groove is provided at the bottom of the droplet collection groove; the through groove exposes the plurality of droplet nozzles.

Optionally, the PCR system further comprises at least one PCR reagent chamber for storing a digital PCR solution; flow channels are provided in the droplet nozzle member, and the droplet nozzles are in communication with the PCR reagent chamber through the flow channels.

Optionally, the flow channels comprise at least one main flow channel and a plurality of branch flow channels connecting to the main flow channel, and each of the droplet nozzles is in communication with one of the branch flow channels, respectively.

Optionally, the digital PCR system further comprises a substrate, the PCR reagent chamber is arranged in the substrate, and the droplet nozzle member is connected above the substrate.

Optionally, the substrate comprises a first substrate component and a second substrate component, and the PCR reagent chamber comprise a PCR reagent upper chamber and a PCR reagent lower chamber, the PCR reagent upper chamber has an opening on the upper surface of the first substrate component and extends through the lower surface of the first substrate component, the PCR reagent lower chamber has an opening on the upper surface of the second substrate component and extending toward, but not through, the lower surface of the second substrate component, and the PCR reagent upper chamber is in communication with and partially overlapped with the PCR reagent lower chamber.

Optionally, at least one digital PCR solution injection hole is provided on the lower surface of the second substrate component, the digital PCR solution injection hole is in communication with the PCR reagent lower chamber.

Optionally, the PCR reagent lower chamber comprises a first end and a second end, the digital PCR solution injection hole is in communication with the PCR reagent lower chamber at the first end, the PCR reagent lower chamber is in communication with the PCR reagent upper chamber at the second end, the PCR reagent lower chamber firstly progressively increased and then gradually decreased in size from the first end to the second end.

Optionally, at least one exhaust port is provided on the lower surface of the second substrate component, the exhaust port is in communication with the PCR reagent upper chamber via a gas passage, the gas passage has an opening on the upper surface of the second substrate component and extends toward, but not through, the lower surface of the second substrate component.

Optionally, the first substrate component is fixed above the second substrate component by gluing.

Optionally, the digital PCR system further comprises a flexible circuit board, the flexible circuit board is connected to above the substrate, a through hole is provided in the flexible circuit board for accommodating the droplet nozzle member, a plurality of first connection pads and a plurality of the second connection pads are arranged on the surface of the flexible circuit board, and the droplet nozzle member is connected to the first connection pads by conducting wires.

Optionally, the flexible circuit board is connected to the substrate by gluing, a channel is provided on the surface of the substrate for preventing glue from flowing to the droplet nozzle member.

Optionally, at least two positioning through holes are arranged in the flexible circuit board, positioning bumps at positions corresponding to the positioning through holes are provided on the surface of the substrate.

Optionally, the digital PCR system further comprises a controller, the controller comprises a controller housing and a controller circuit board arranged in the controller housing, the controller housing has a support for placing the substrate, a plurality of conductive pins for circuit connection connected to the circuit connection board of the controller are arranged on the surface of the support, said conductive pins for circuit connection are at positions corresponding to the second connection pads.

Optionally, at least one position-limiting slot is provided at one end of the substrate, and at least one position-limiting part corresponding to the position-limiting slot is provided in the controller housing.

Optionally, a position-limiting through hole is provided in the substrate, the position-limiting through hole penetrates the front surface and the back surface of the substrate, and a position-limiting part corresponding to the position-limiting slot is provided in the controller housing.

Optionally, a material of the substrate comprises plastic or glass.

The present invention also provides a method for generating digital PCR droplets, comprising the following steps of: a digital PCR solution is vaporized by using vaporizing parts and rapidly pushed into droplet generating oil to form digital PCR droplets.

Optionally, the vaporizing parts comprise heating elements for vaporizing liquid layers of the digital PCR solution by heating.

Optionally, a generation rate of the digital PCR droplets is controlled by controlling the heating time, the number of heatings and the time intervals of heating of the heating elements.

Optionally, comprising the following steps of:
injecting a digital PCR solution into a PCR reagent chamber, so that the digital PCR solution enters droplet nozzles in communication with the PCR reagent chamber to form liquid layers of the digital PCR solution;
adding droplet generating oil into the droplet collection groove;
the liquid layers are vaporized by using the vaporizing parts and rapidly pushed into the droplet generating oil in the droplet collection groove to generate the digital PCR droplets.

Optionally, the thickness of the liquid layer is in the range of 0.2 nm to 30,000 nm.

Optionally, the digital PCR droplets are generated at a rate of more than 1000 droplets per second.

As described above, the digital PCR system and the method for generating digital PCR droplets of the present invention have the following beneficial effects:

(1) Thermal bubble technique is used in the present invention for high-speed digital PCR droplet generation. The rapid droplet generation relies on the instantaneous heating and vaporization of liquid layers with a thickness in nanometer-scale by using vaporizing parts in droplet nozzles, so that the digital PCR solution inside the droplet nozzles is rapidly pushed into droplet generating oil to generate digital PCR droplets. Compared with the generation rate of 100 droplets per second on the market, a droplet generation speed of more than 1000 drops per second can be achieved by the droplet generation technique of the present invention.

(2) Compared with the method by which the oil and water phases move together to generate droplets, the oil phase in the technical solution of the present invention is static, so the consumption of oil is greatly reduced, reducing the amount of oil by about 50%.

Figure 1A:
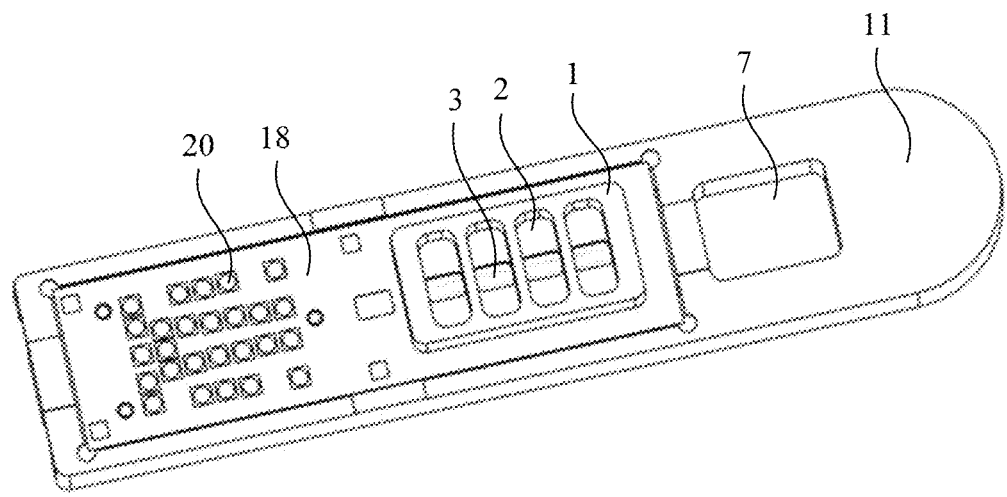
FIG. 1a is a perspective view of the digital PCR system of the present invention.

LIST OF REFERRINGENCE NUMERALS 1 droplet generation component
2 droplet collection groove
3 droplet nozzle member
4 droplet nozzle
5 vaporizing part
6 through groove
7 position-limiting hole
8 gas passage
9 main flow channel
10 branch flow channel
11 substrate
12 first substrate component
13 second substrate component
14 PCR reagent upper chamber
15 PCR reagent lower chamber
16 digital PCR solution injection hole
17 exhaust port
18 flexible circuit board
19 through hole
20 second connection pad
21 channel
22 positioning through hole
23 positioning bump
24 controller
25 controller housing
26 support
27 conductive pin for circuit connection
28 position-limiting slot
29, 30 position-limiting part
31 protuberance

DETAILED DESCRIPTION OF THE PRESENT INVENTION

Hereinafter, the embodiments of the present invention will be illustrated with specific examples, and other advantages and benefits of the present invention can be readily understood by those skilled in the art as disclosed in this specification. The present invention may also be implemented or applied with various other specific embodiments, and the details in this specification may be modified or altered in various ways based on different points of view and applications without departing from the spirit of the present invention.

Referring to FIG. 1a to FIG. 12. It should be noted that the illustrations provided in the examples only illustrate the basic concept of the present invention in a schematic manner, and that the drawings only show the components related to the present invention rather than the numbers, shapes and sizes of the components in actual implementation, and that the shape, number and ratio of each component in actual implementation may be changed arbitrarily, and the types of layout pattern of the components may be also more complicated.

Embodiment 1

Figure 1B:
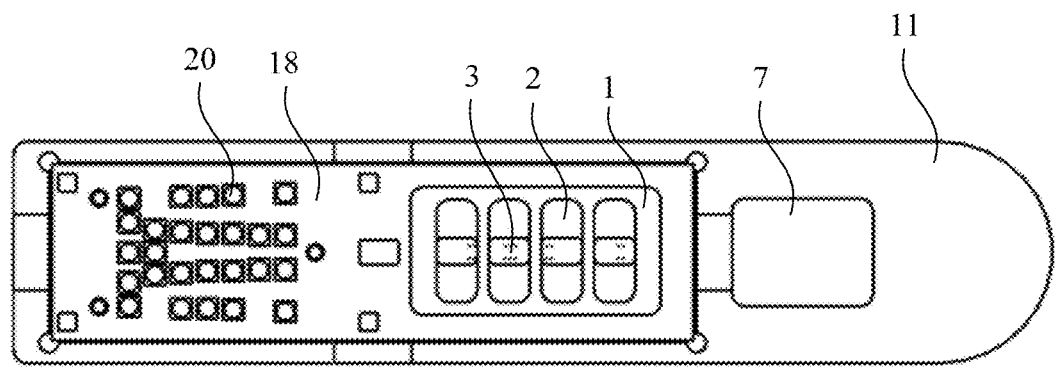
FIG. 1b is a top view of the digital PCR system of the present invention.
Figure 1C:
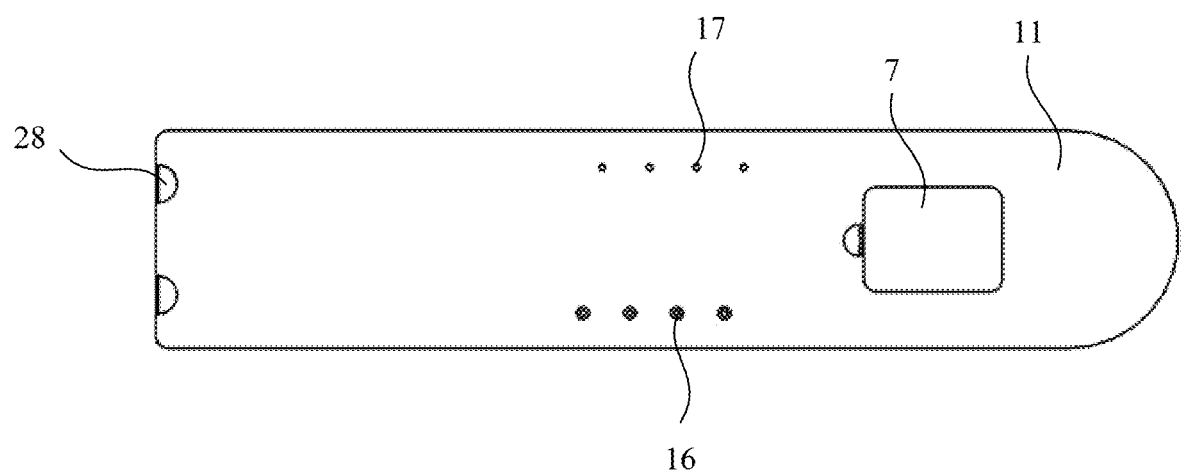
FIG. 1c is a bottom view of the digital PCR system of the present invention.
Figure 1D:
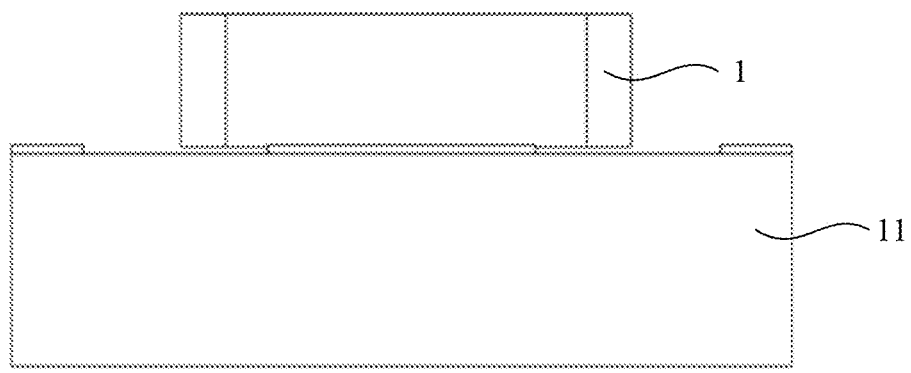
FIG. 1d to FIG. 1g are side views of the digital PCR system.
Figure 1E:
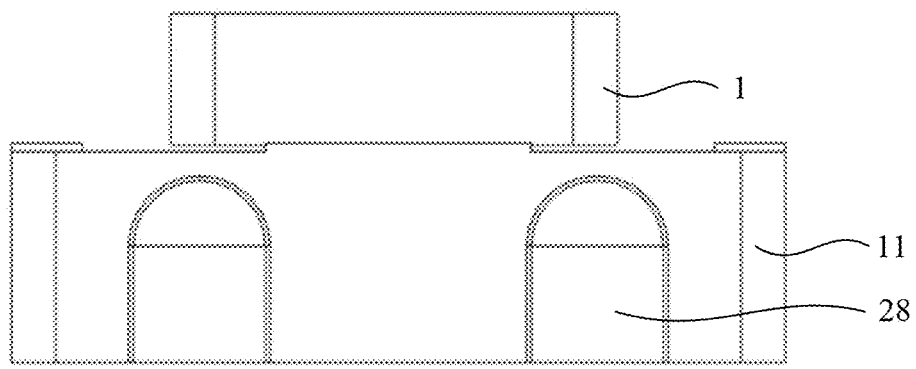
Figure 1F:
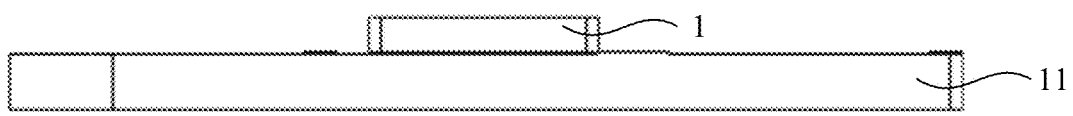
Figure 1G:
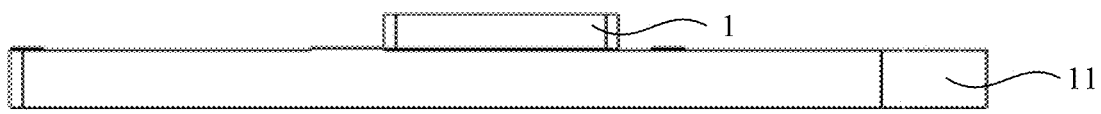
Figure 2:
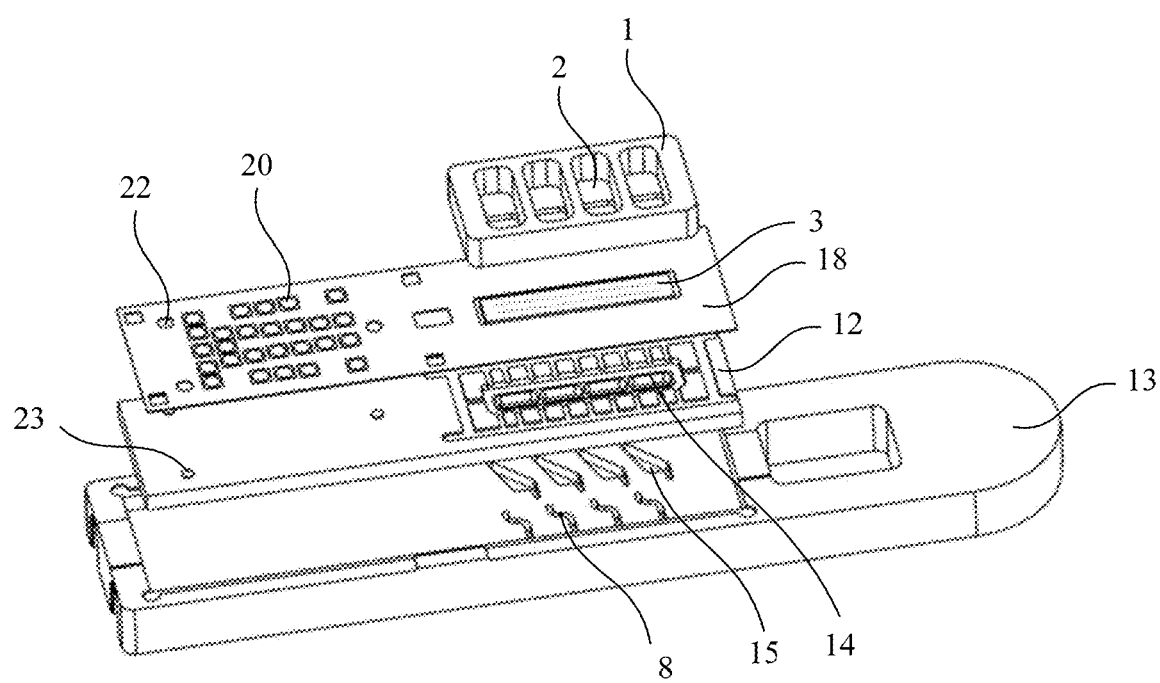
FIG. 2 is an exploded view of the digital PCR system of the present invention.

The present invention provides a digital PCR system, as shown in FIG. 1a to FIG. 1g, among them, FIG. 1a is a perspective view of the digital PCR system, FIG. 1b displays a top view of the digital PCR system, FIG. 1c shows a bottom view of the digital PCR system, and FIG. 1d, FIG. 1e, FIG. 1f, and FIG. 1g are side views of the digital PCR system in four directions, respectively. FIG. 2 is an exploded view of the digital PCR system, in this embodiment, the digital PCR system comprises at least one droplet generation component 1 and a droplet nozzle member 3, the droplet nozzle member 3 is connected below the droplet generation component 1.

Specifically, the droplet generation component 1 comprises at least one droplet collection groove 2. FIG. 1a shows that the number of the droplet generation component 1 is one, and the droplet generation component 1 comprises four droplet collection grooves 2, wherein each droplet collection groove 2 is arranged in a row and two adjacent droplet collection grooves 2 share a common sidewall. Of course, in other embodiments, a plurality of droplet collection grooves 2 may also be arranged in other ways and may be arranged separately, the number of droplet generation components 1 may also be plural, and the scope of protection of the present invention should not be unduly limited herein.

Figure 3:
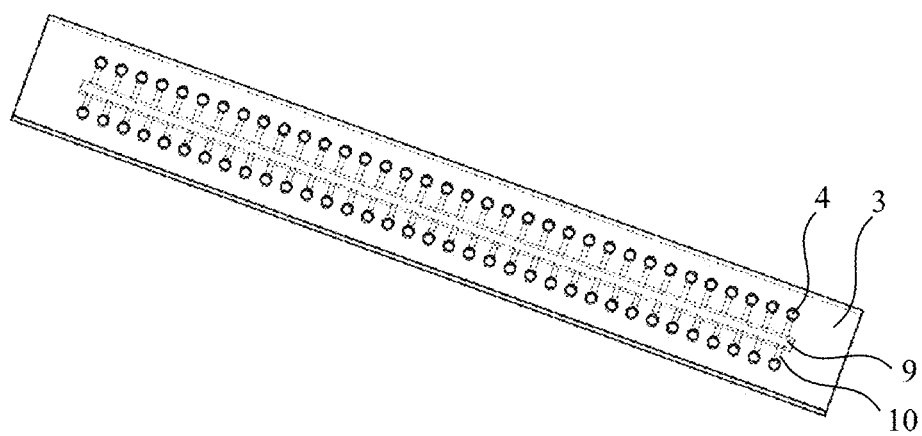
FIG. 3 is a perspective view of the droplet nozzle member in the digital PCR system of the present invention.

Referring to FIG. 3, it shows a perspective view of droplet nozzle member 3, the droplet nozzle member 3 comprises a plurality of droplet nozzles 4. In the embodiment, droplet nozzles 4 are arranged in two rows and the droplet nozzles is evenly distributed in each row. In other embodiments, the droplet nozzles 4 may also be arranged in other ways, and the scope of protection of the present invention should not be unduly limited herein.

Figure 4:
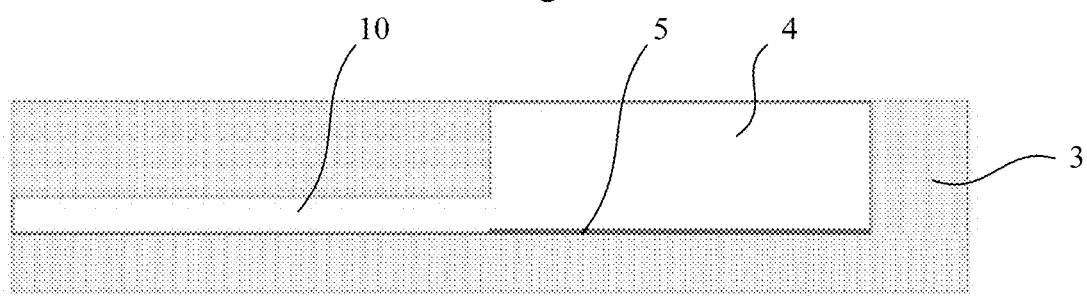
FIG. 4 is a partial cross-sectional view of the droplet nozzle member in the digital PCR system of the present invention.

Referring to FIG. 4, it shows a partial cross-sectional view of the droplet nozzle member 3. In the embodiment, the droplet nozzles 4 have openings on the upper surface of droplet nozzle member 3, and extend toward, but not through, the lower surface of droplet nozzle member 3. The shape of the opening of each of droplet nozzles 4 comprises, but is not limited to, any one selected from the group consisting of round, ellipse and polygon. The volume of the digital PCR droplet to be generated is determined by the volume of the droplet nozzle 4.

As an example, the droplet nozzle member 3 may comprise thermal bubble print chips. Thermal bubble print technique is a major technique in the field of printers, the basic principle of the thermal bubble print technique is to eject ink droplets by heating ink. In the present invention, droplet nozzle member 3 may use existing thermal bubble print chips.

Figure 5A:
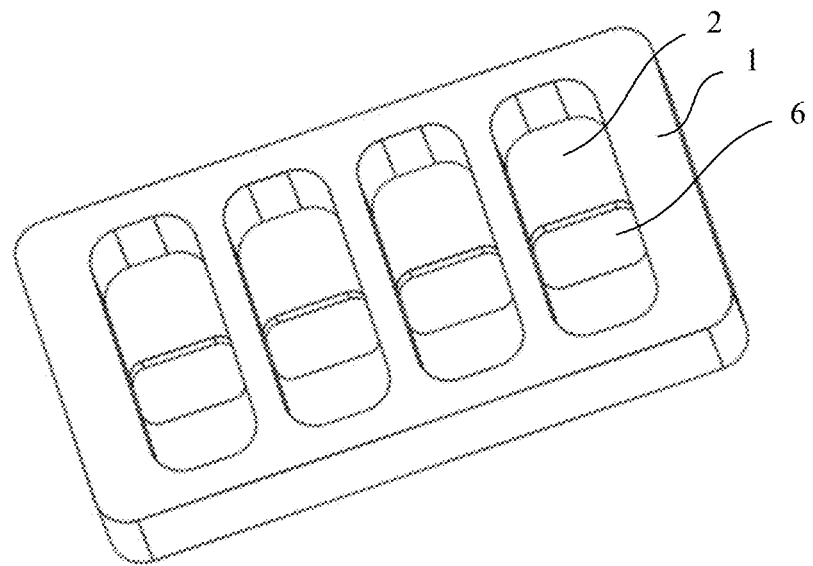
FIG. 5a is a front perspective view of the droplet generation component in the digital PCR system of the present invention.
Figure 5B:
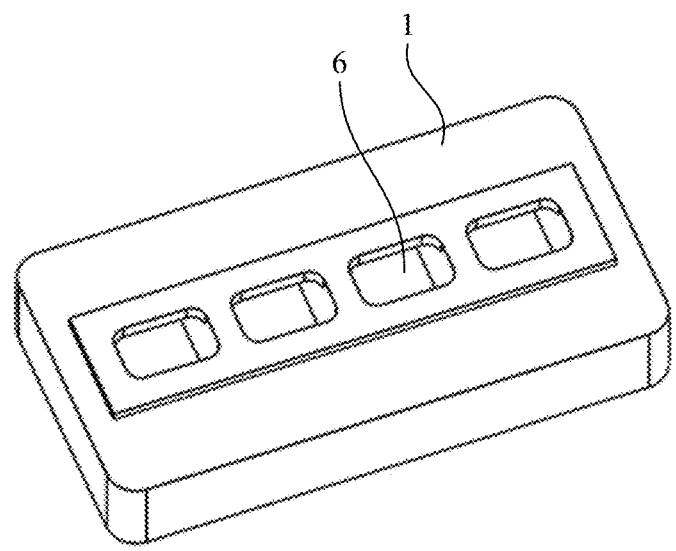
FIG. 5b is a back perspective view of the droplet generation component in the digital PCR system of the present invention.
Figure 5C:
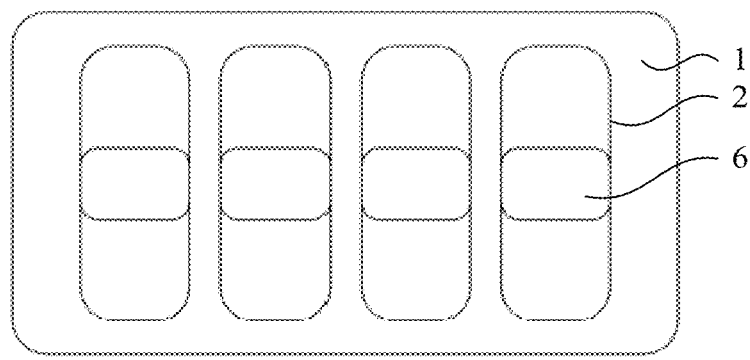
FIG. 5c is a top view of the droplet generation component in the digital PCR system of the present invention.
Figure 5D:
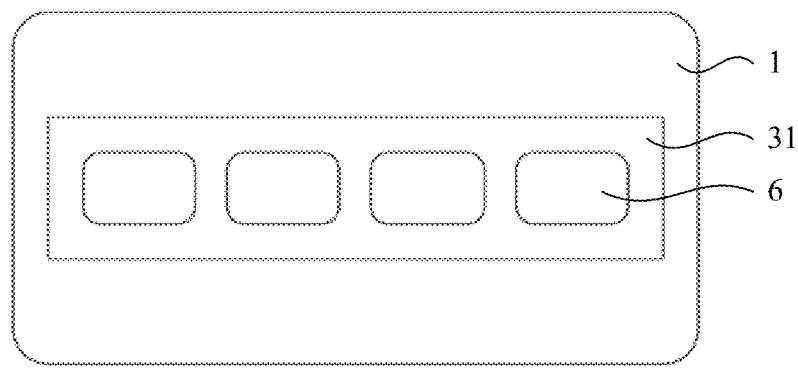
FIG. 5d is a bottom view of the droplet generation component in the digital PCR system of the present invention.
Figure 5E:
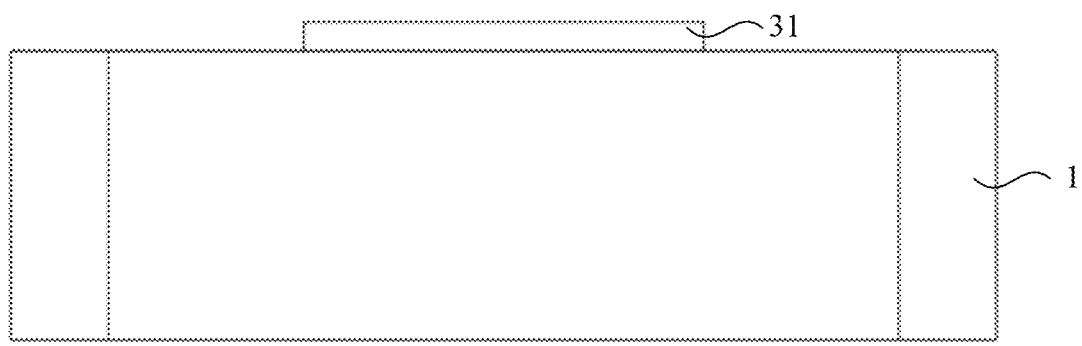
FIG. 5e to FIG. 5h are side views of the droplet generation component in the digital PCR system of the present invention.
Figure 5F:
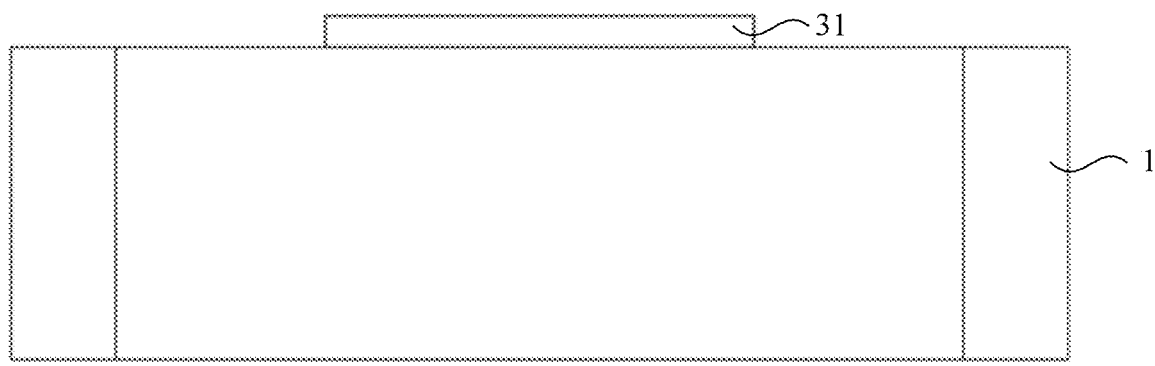
Figure 5G:
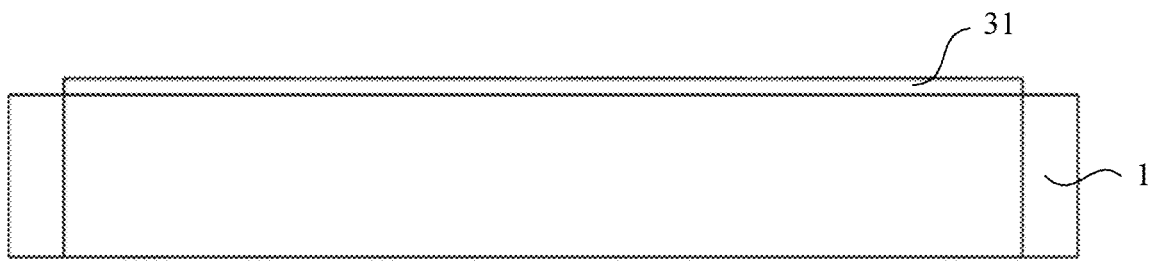
Figure 5H:
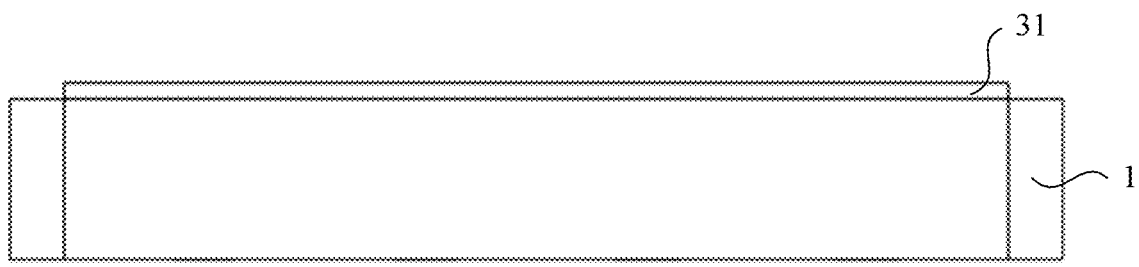

Referring to FIG. 5a to FIG. 5h, wherein, FIG. 5a is a front perspective view of the droplet generation component 1, FIG. 5b is a back perspective view of the droplet generation component 1, FIG. 5c is a top view of the droplet generation component 1, FIG. 5d is a bottom view of the droplet generation component 1, and FIG. 5e, FIG. 5f, FIG. 5g and FIG. 5h are side views of the droplet generation component 1 in four directions, respectively. In the embodiment, a through groove 6 is provided at the bottom of the droplet collection groove to expose a plurality of droplet nozzles 4, so that the droplet nozzles 4 are in communication with the droplet collection groove 2.

Specifically, as shown in FIG. 4, the droplet nozzle 4 is provided with a vaporizing part 5 for vaporizing liquid layers of the digital PCR solution inside the droplet nozzle and the vaporized solution is rapidly pushed into the droplet generating oil in the droplet collection groove 2 to generate digital PCR droplets.

As an example, the vaporizing part 5 is arranged on the bottom of droplet nozzle 4, and the vaporizing part 5 comprises a heating element for vaporizing the liquid layers of the digital PCR solution by heating. In the embodiment, the heating element comprises a heating plate, which may either a single metal layer or a composite multilayer metal layer. The shape of vaporizing part 5 comprises, but is not limited to, a round or square shape, and the area thereof may be 0.5 to 2 times the area of the bottom of the droplet nozzle 4. In other embodiments, the vaporizing part 5 may also be arranged on the sidewall of the droplet nozzle 4, and the scope of protection of the present invention should not be unduly limited herein.

Specifically, the PCR system further comprises at least one PCR reagent chamber for storing a digital PCR solution. As shown in FIG. 3 and FIG. 4, flow channels are provided in the droplet nozzle member 3, and the droplet nozzles 4 are in communication with the PCR reagent chamber through the flow channels.

As an example, the flow channels comprise at least one main flow channel 9 and a plurality of branch flow channels 10 in communication with the main flow channel 9, and each of the droplet nozzles 4 is in communication with one of the branch flow channels 10, respectively. FIG. 3 displays that the droplet nozzle member 3 comprises one main flow channel 9. In other embodiments, the number of the main flow channels 9 may also match the number of the droplet collection grooves 2. For example, as shown in FIG. 10b, the droplet nozzle member 3 comprises four main flow channels 9.

As an example, materials for constructing the flow channels and the droplet nozzles comprise, but are not limited to, silicon, polymers, photoresists, etc.

Specifically, as shown in FIG. 1a, the digital PCR system further comprises a substrate 11, the PCR reagent chamber is arranged in the substrate 11, and the droplet nozzle member 3 is connected above the upper surface of substrate 11.

As an example, a material for substrate 11 comprises, but is not limited to, any one of a transparent or opaque plastic, glass.

As an example, as shown in FIG. 2, the substrate 11 comprises a first substrate component 12 and a second substrate component 13, and the PCR reagent chamber comprises a PCR reagent upper chamber 14 and a PCR reagent lower chamber 15; the PCR reagent upper chamber 14 has an opening on the upper surface of the first substrate component 12 and extends through the lower surface of the first substrate component 12, the PCR reagent lower chamber 15 has an opening on the upper surface of the second substrate component 13 and extends toward, but not through, the lower surface of the second substrate component 13, and the PCR reagent upper chamber 14 is in communication with and partially overlapped with the PCR reagent lower chamber 15.

Figure 6A:
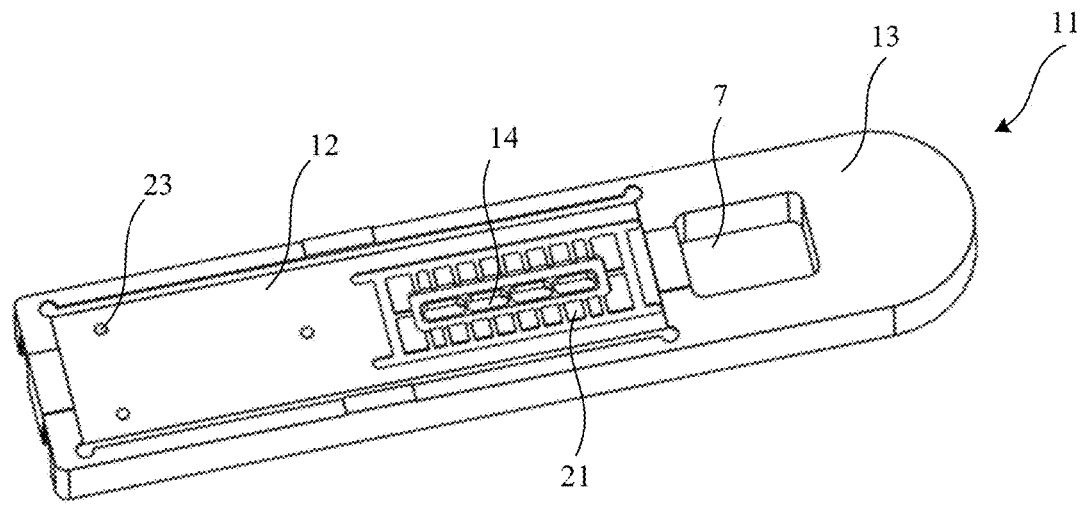
FIG. 6a is a perspective view of the substrate in the digital PCR system of the present invention.
Figure 6B:
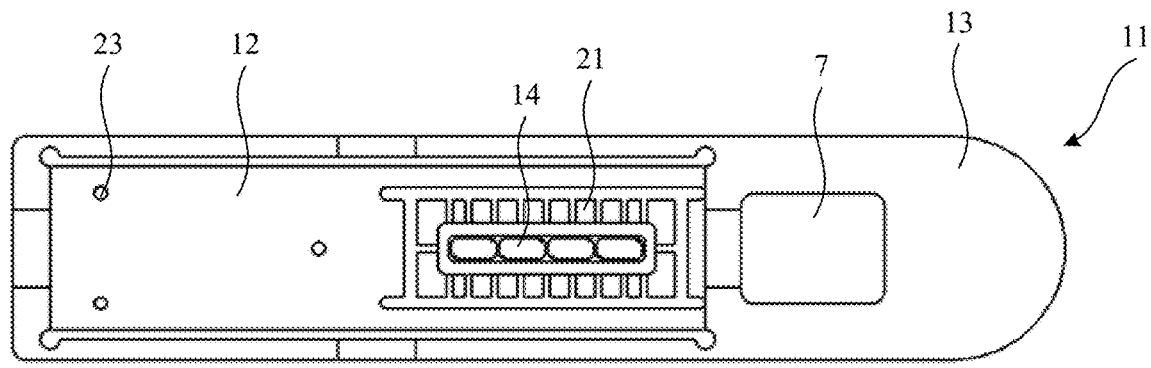
FIG. 6b is a top view of the substrate in the digital PCR system of the present invention.
Figure 6C:
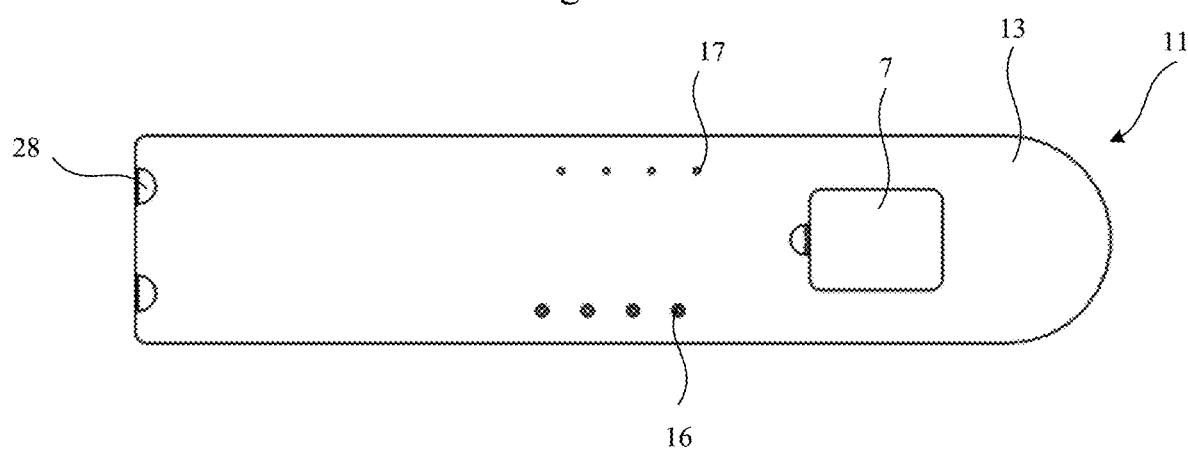
FIG. 6c is a bottom view of the substrate in the digital PCR system of the present invention.
Figure 6D:
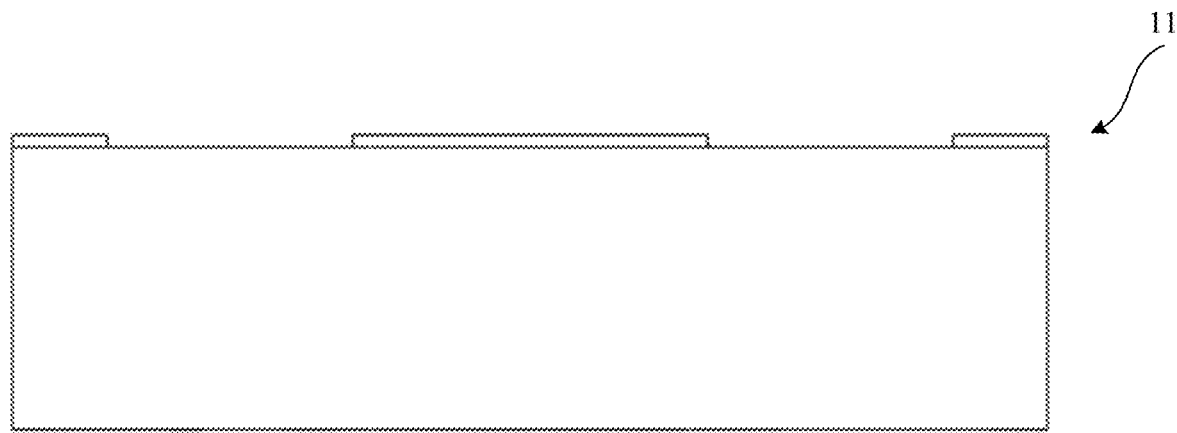
FIG. 6d to FIG. 6g are side views of the substrate in the digital PCR system of the present invention.
Figure 6E:
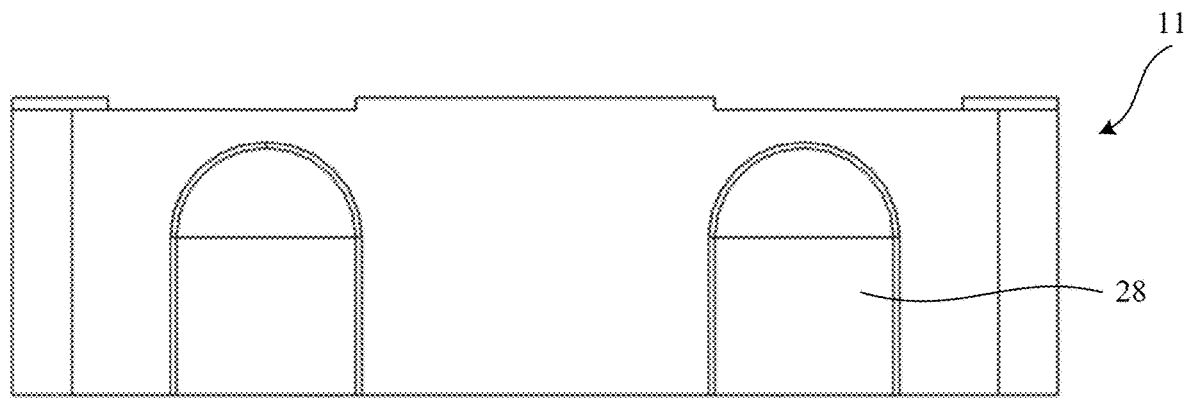
Figure 6F:
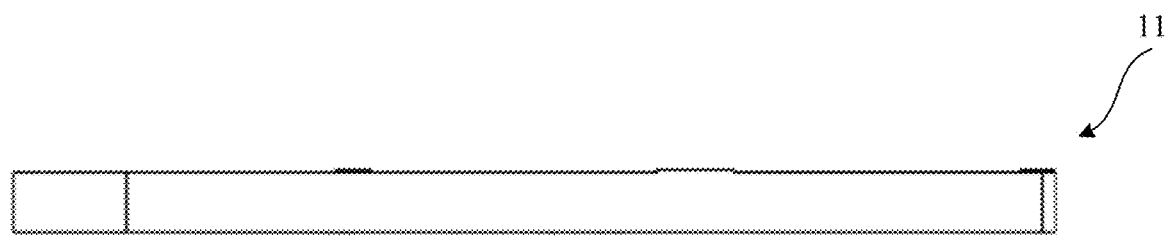
Figure 6G:
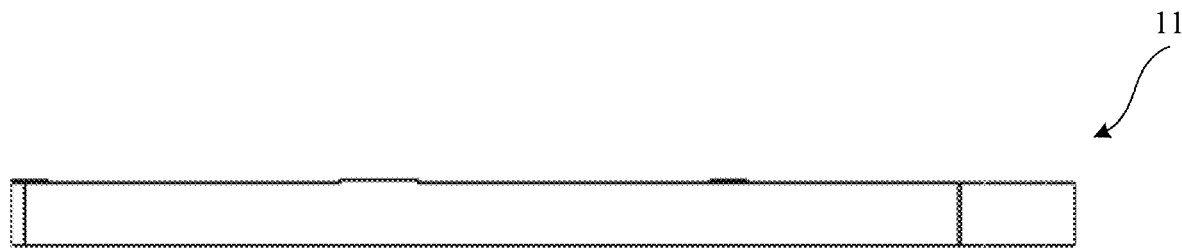

Referring to FIG. 6a to FIG. 6g, among them, FIG. 6a is a perspective view of substrate 11, FIG. 6b is a top view of substrate 11, FIG. 6c is a bottom view of substrate 11, and FIG. 6d, FIG. 6e, FIG. 6f and FIG. 6g are side views of substrate 11 in four directions, respectively.

As an example, the first substrate component 12 is fixed above the second substrate component 13 by gluing, e.g. with double-sided tapes or glue. In the embodiment, a sunken platform is provided on the surface of the second substrate component 13 for accommodating second substrate component 13, and arc-shaped extended spaces are provided at the four corners of the sunken platform, and the protrusions around the sunken platform function as a means for positioning when first substrate component 12 is glued to the sunken platform surface.

Figure 7:
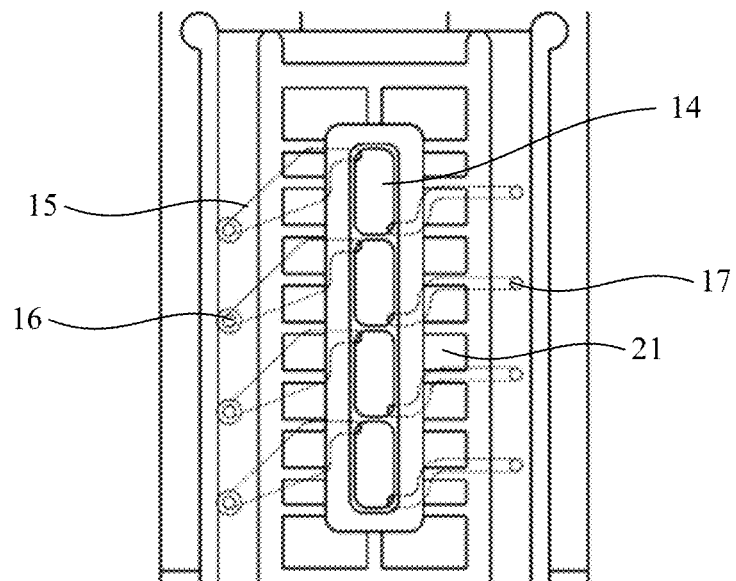
FIG. 7 is a partial top view of the substrate in the digital PCR system of the present invention.

Referring to FIG. 7, it is a partial top view of the substrate, wherein it shows the relative position relationship between the PCR reagent upper chambers 14 and the PCR reagent lower chambers 15. In the embodiment, the PCR reagent is divided into two parts in order to hold enough digital PCR solution.

Figure 8:
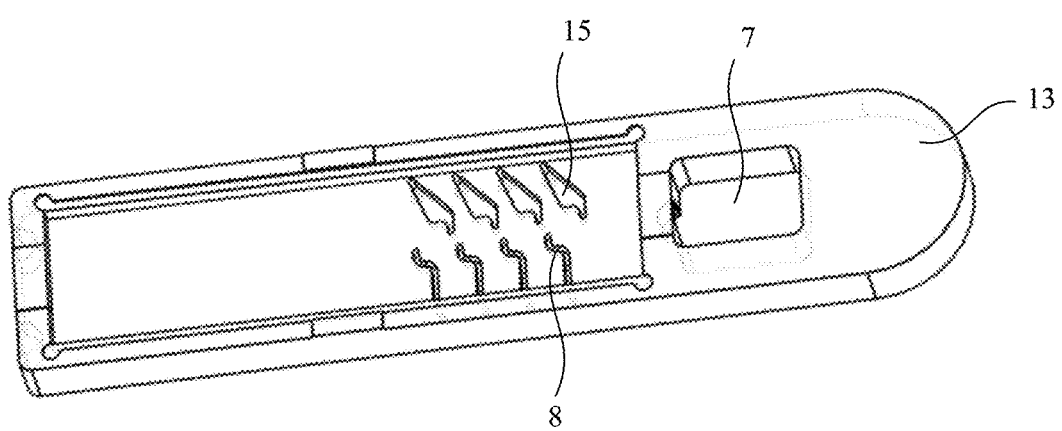
FIG. 8 is a front perspective view of the second substrate component in the digital PCR system of the present invention.
Figure 9:
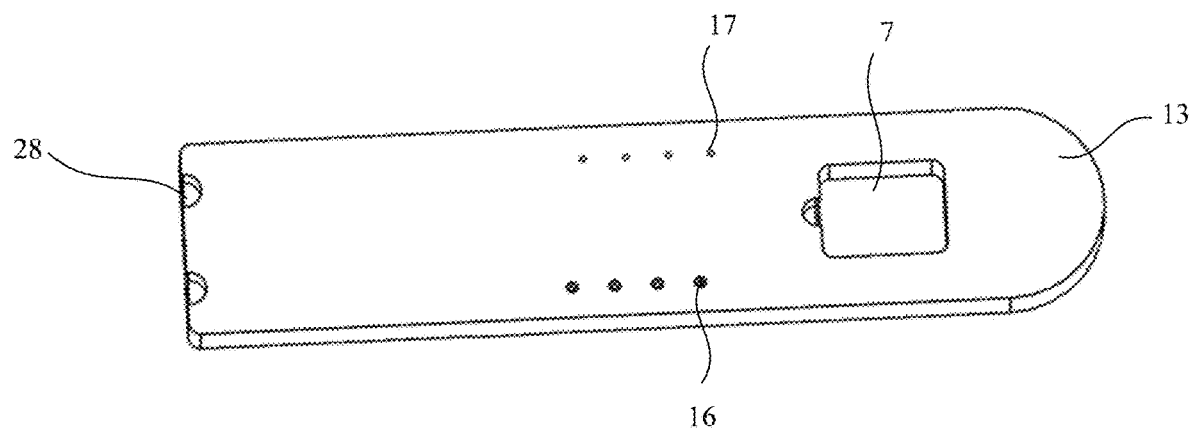
FIG. 9 is a back perspective view of the second substrate component in the digital PCR system of the present invention.

Referring to FIG. 8 and FIG. 9, they are front and back perspective views of the second substrate component 13, respectively. As shown in FIG. 7 and FIG. 9, in the embodiment, at least one digital PCR solution injection hole 16 is provided on the lower surface of the second substrate component 13, and digital PCR solution injection hole 16 is in communication with the PCR reagent lower chamber 15, for injecting the digital PCR solution into the PCR reagent chamber through the digital PCR solution injection hole 16.

Specifically, as shown in FIG. 7 and FIG. 8, the PCR reagent lower chamber 15 comprises a first end and a second end, the digital PCR solution injection hole 16 is in communication with the PCR reagent lower chamber 15 at the first end, the PCR reagent lower chamber 15 is in communication with the PCR reagent upper chamber 14 at the second end. In the embodiment, the PCR reagent lower chamber 15 is firstly progressively increased and then gradually decreased in size from the first end to the second end. With this design, it can prevent the formation of bubbles when adding liquid.

Specifically, as shown in FIG. 7 and FIG. 9, at least one exhaust port 17 is provided on the lower surface of the second substrate component 13, and the exhaust port 17 is in communication with the PCR reagent upper chamber 14 via a gas passage 8. As shown in FIG. 8, the gas passage 8 has an opening on the upper surface of the second substrate component 13 and extends toward, but not through, the lower surface of the second substrate component 13.

Specifically, in the embodiment, the opening area of the digital PCR solution injection hole 16 is greater than the opening area of the exhaust port 17, and the opening area of the digital PCR solution injection hole 16 is prepared slightly larger to support the tips of the pipetting gun. Due to capillarity, the liquid injected into the PCR reagent chamber does not flow out from the digital PCR solution injection hole 16 or the exhaust port 17.

Specifically, as shown in FIG. 1a and FIG. 2, the digital PCR system further comprises a flexible circuit board 18, the flexible circuit board 18 is connected to the upper surface of the substrate 11, and the droplet nozzle member 3 is connected in flexible circuit board 18.

Figure 10A:
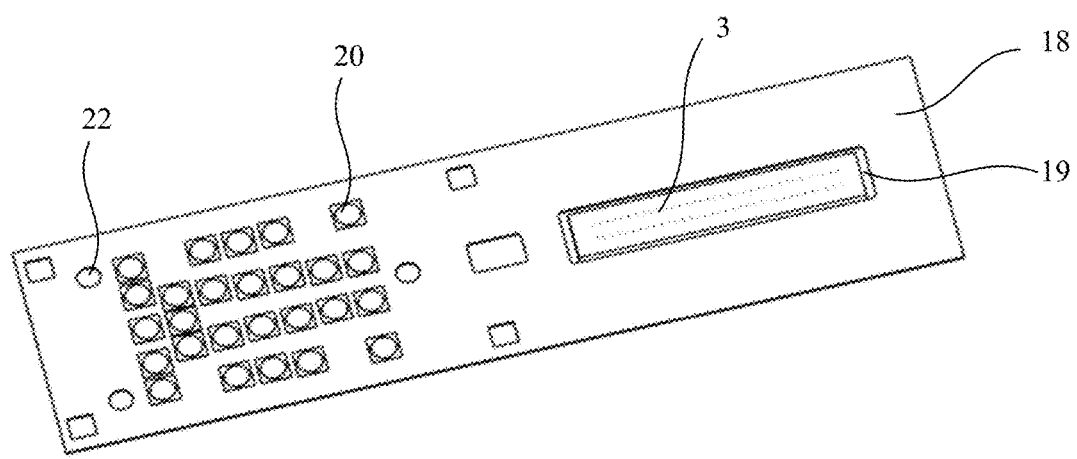
FIG. 10a is a front perspective view of the droplet nozzle member connected to the flexible circuit board in the digital PCR system of the present invention.
Figure 10B:
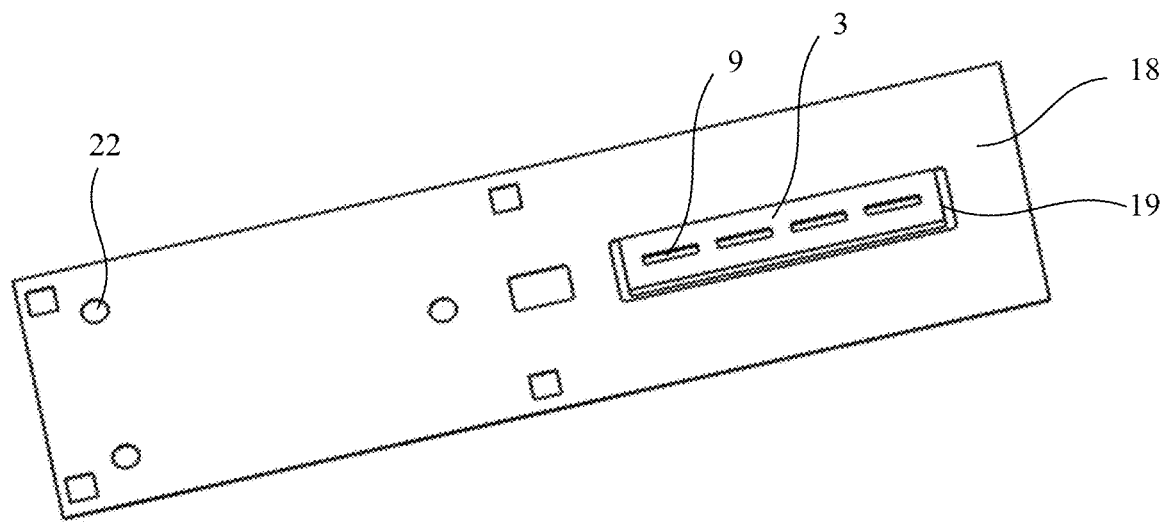
FIG. 10b is a back perspective view of the droplet nozzle member connected to the flexible circuit board in the digital PCR system of the present invention.
Figure 10C:
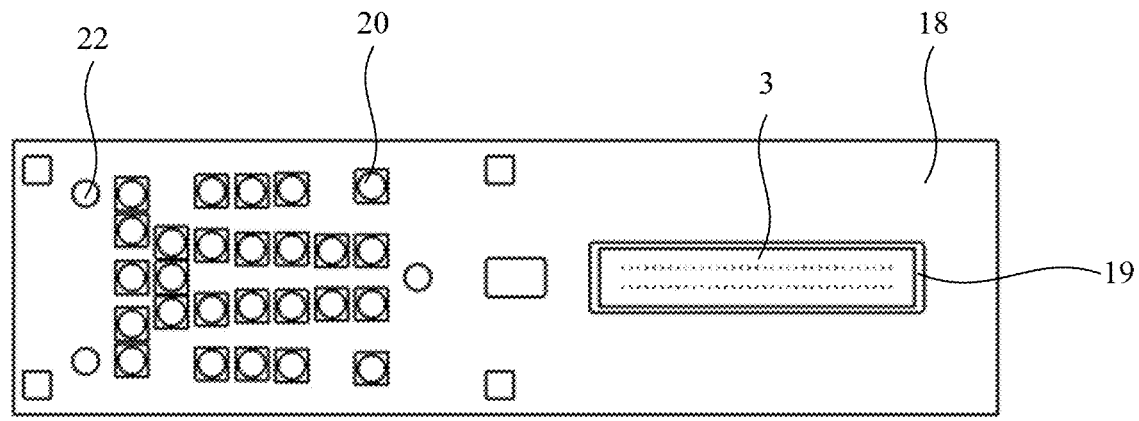
FIG. 10c is a top view of the droplet nozzle member connected to the flexible circuit board in the digital PCR system of the present invention.
Figure 10D:
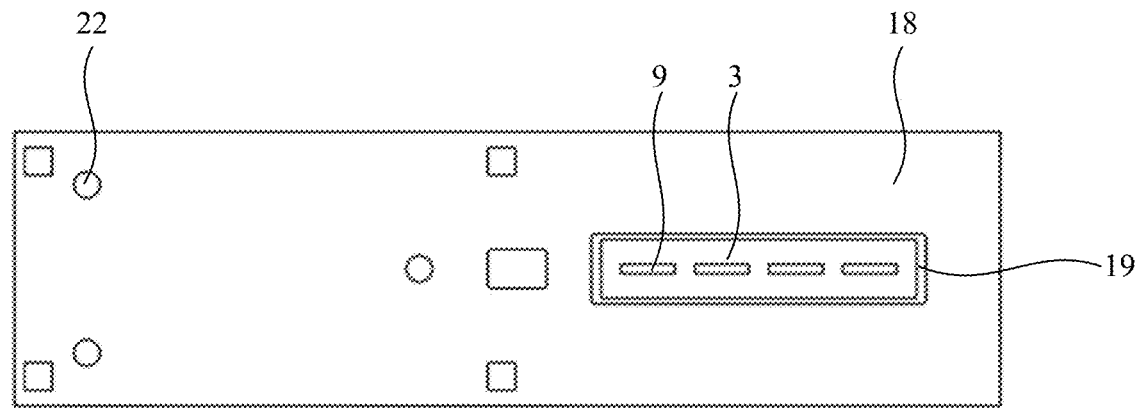
FIG. 10d is a bottom view of the droplet nozzle member connected to the flexible circuit board in the digital PCR system of the present invention.
Figure 10E:
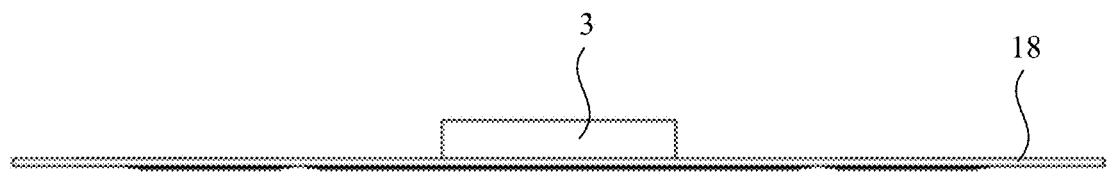
FIG. 10e to FIG. 10h are side views of the droplet nozzle member connected to the flexible circuit board in the digital PCR system of the present invention.
Figure 10F:
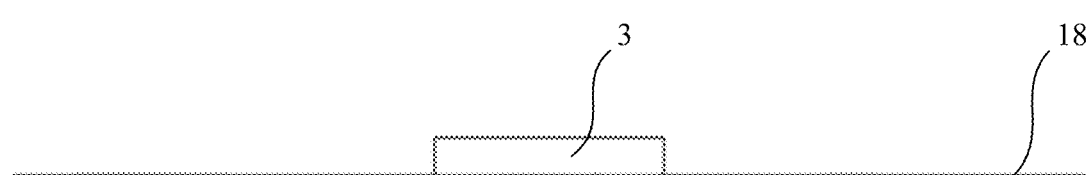
Figure 10G:
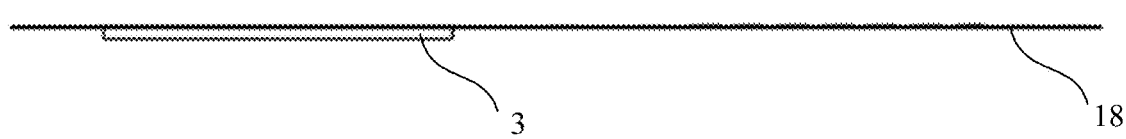
Figure 10H:

Referring to FIG. 10a to FIG. 10h, wherein, FIG. 10a is a front perspective view of the droplet nozzle member 3 connected to the flexible circuit board 18; FIG. 10b is a back perspective view of the droplet nozzle member 3 connected to the flexible circuit board 18; FIG. 10c is a top view of the droplet nozzle member 3 connected to the flexible circuit board 18; FIG. 10d is a bottom view of droplet nozzle member 3 connected to the flexible circuit board 18; and FIG. 10e, FIG. 10f, FIG. 10g, and FIG. 10h are side views of the droplet nozzle member 3 connected to the flexible circuit board 18 in four directions, respectively.

Specifically, a through hole 19 is provided in the flexible circuit board 18 for accommodating the droplet nozzle member 3, a plurality of the first connection pads (not shown) and the second connection pads 20 are arranged on the surface of the flexible circuit board 18, the droplet nozzle member 3 is connected to the first connection pads by conducting wires, and the vaporizing parts 5 are connected to an external controller via flexible circuit board 18. The droplet nozzle member 3 is connected to the first connection pads by using a standard Wire Bond process.

As an example, the flexible circuit board 18 is connected to the substrate 11, as shown in FIG. 6a, the channels 21 are provided on the surface of the substrate 11 for preventing glue from flowing to the droplet nozzle member 3. The number of channels 21 is plural, and the channel distributes around the droplet nozzle member 3. The arrangement of channels 21 may be adjusted as required, and is not limited to the arrangement shown in FIG. 6a.

Specifically, the droplet generation component 1 is fixed on the flexible circuit board 18 by gluing. As shown in FIG. 5b, a protuberance 31 is arranged on the back of the droplet generation component 1, which ensures a strong bonding between the droplet generation component 1 and the flexible circuit board 18.

Specifically, as shown in FIG. 10a and FIG. 10b, at least two positioning through holes 22 are arranged in the flexible circuit board 18. As shown in FIG. 6a, the positioning bumps 23 at positions corresponding to the positioning through holes 22 are provided on the surface of the substrate 11. The positioning through holes 22 engage with the positioning bumps 23 to facilitate the accurate positioning of the flexible circuit board 18 on the substrate 11.

Figure 11:
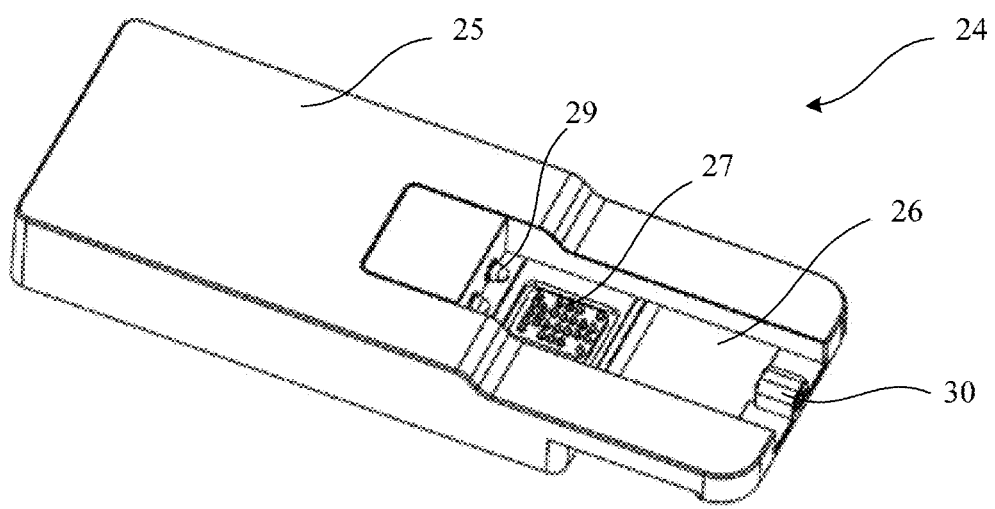
FIG. 11 is a perspective view of the controller in the digital PCR system of the present invention.

Specifically, the digital PCR system further comprises a controller. As shown in FIG. 11, it shows a perspective view of controller 24, which comprises a controller housing 25 and a controller circuit board arranged in the controller housing 25. The controller housing 25 has a support 26 for placing the substrate 11, a plurality of conductive pins for circuit connection 27 (also known as Pin) connected to the circuit connection board of the controller are arranged on the surface of support 26, and the conductive pins for circuit connection 27 are at positions corresponding to the second connection pads 30 on the flexible circuit board 18.

Specifically, the controller 24 is connected to the droplet nozzle member 3 via the flexible circuit board 18. The generation rate of the digital PCR droplets is controlled by controlling the heating time, the number of heatings and the time intervals of heating of the heating elements. Wherein, the control circuit of the controller 24 may employ an existing circuit structure.

Specifically, as shown in FIG. 9, at least one position-limiting slot 13 is provided at one end of the substrate, and as shown in FIG. 11, at least one position-limiting part 29 corresponding to the position-limiting slot 13 is provided in the controller housing 25.

Further, as shown in FIG. 8 and FIG. 9, a position-limiting hole 7 is provided in the substrate, the position-limiting hole 7 penetrates the front surface and the back surface of the substrate, and as shown in FIG. 11, a position-limiting part 30 corresponding to the position-limiting slot 7 is provided in the controller housing 25.

The digital PCR system of the present invention can be used for generating digital PCR droplets. The rapid droplet generation relies on the instantaneous vaporization of liquid layers with a thickness in nanometer-scale by using vaporizing parts in the droplet nozzles, so that the digital PCR solution inside the droplet nozzles is rapidly pushed into droplet generating oil to generate digital PCR droplets. Compared with the generation rate of 100 droplets per second on the market, a droplet generation rate of more than 1000 drops per second can be achieved by the droplet generation technique of the present invention. Compared with the method by which the oil and water phases move together to generate droplets, the oil phase in the technical solution of the present invention is static, so the consumption of oil is greatly reduced, reducing the amount of oil by about 50%. The technical solution of the present invention has an efficient utilization rate of digital PCR oil.

Embodiment 2

The present invention also provides a method for generating digital PCR droplets, comprising the following steps of: the digital PCR solution is vaporized by using vaporizing parts and rapidly pushed into droplet generating oil to generate digital PCR droplets.

As an example, the thermal bubble technique is used for high-speed digital PCR droplet generation. The vaporizing parts comprise heating elements for vaporizing the liquid layers of the digital PCR solution by heating.

Specifically, the generation rate of the digital PCR droplets is controlled by controlling the heating time, the number of heatings and the time intervals of heating of the heating element. The digital PCR droplet generation at a rate of more than 1000 droplets per second can be achieved by the method for generating digital PCR droplets of the present invention.

As an example, the method for generating digital PCR droplets comprises the following steps of:
S1: injecting a digital PCR solution into a PCR reagent chamber, so that the digital PCR solution enters the droplet nozzles in communication with the PCR reagent chamber to form liquid layers of the digital PCR solution;
S2: adding droplet generating oil into a droplet collection groove;
S3: the liquid layers are vaporized by using the vaporizing parts and rapidly pushed into the droplet generating oil in the droplet collection groove to generate the digital PCR droplets.

Specifically, the thicknesses of the liquid layers are in nanometer scale, and larger than 0.2 nm. In the embodiment, the thicknesses of the liquid layers are in the range of 0.2 nm to 30,000 nm.

Figure 12:
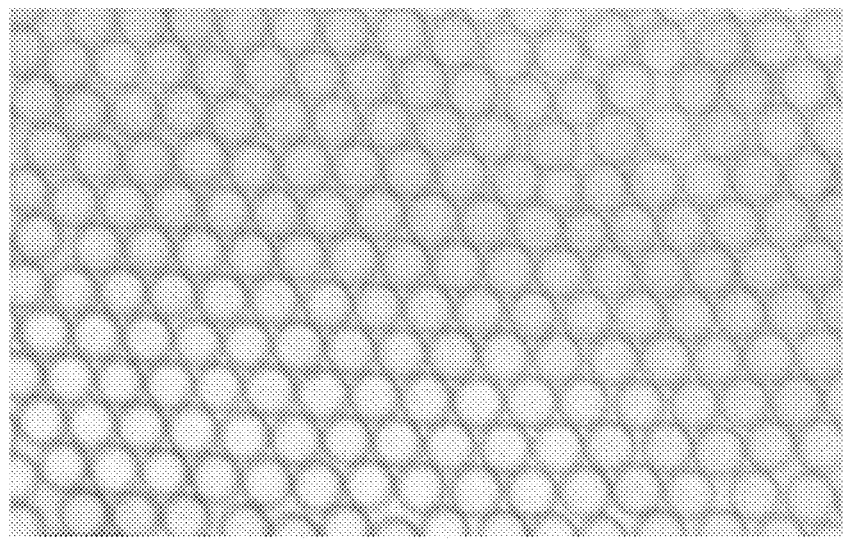
FIG. 12 is an optical microscope image of the digital PCR droplets generated by using the digital PCR system of the present invention.

Referring to FIG. 12, it is an optical microscope image of the digital PCR droplets generated by using the digital PCR system of the present invention, showing that the generated digital PCR droplets are symmetric and uniform in profile.

All of digital PCR biochemical reagents can be utilized when using the digital PCR system and the method for generating digital PCR droplets of the present invention. The concentration of many biomarker molecules in the blood is very low (e.g., circulating tumor DNA has only 3 DNA molecules per 2 ml of blood), but the digital PCR system and the method for generating digital PCR droplets of the present invention have the characteristics that the number of generated droplets is not limited by the amount of oil used and it is high speed, thus making it possible for the application of such assays in digital PCR.

In conclusion, thermal bubble technique is used in the digital PCR system and the method for generating digital PCR droplets of the present invention for high-speed digital PCR droplet generation. The rapid droplet generation relies on the instantaneous heating and vaporization of the liquid layers with a thickness in nanometer-scale by using the vaporizing parts in the droplet nozzles, so a digital PCR solution inside the droplet nozzles is quickly pushed into droplet generating oil to generate digital PCR droplets. Compared with the generation rate of 100 droplets per second on the market, a droplet generation rate of more than 1000 drops per second can be achieved by the droplet generation technique of the present invention. Compared with the method by which the oil and water phases move together to generate droplets, the oil phase in the technical solution of the present invention is static, so the consumption of oil is greatly reduced, reducing the amount of oil by about 50%. The technical solution of the present invention has an efficient utilization rate of digital PCR oil. Therefore, the present invention effectively overcomes various shortcomings in the prior art and has a high utility value in industry.

The above-mentioned embodiments only illustrate the principle and efficacy of the present invention, and are not intended to limit the present invention. The above embodiments may be modified or altered by any person skilled in the art without departing from the spirit and scope of the present invention. Therefore, all equivalent modifications or alterations made by those with ordinary knowledge in the technical field, without departing from the spirit and technical ideas disclosed in the present invention, should still be covered by the claims of the present invention.

The invention claimed is:

1. A digital PCR system, comprising:
   at least one droplet generation component comprising at least one droplet collection groove;
   a droplet nozzle member connected to the droplet generation component and comprising a plurality of droplet nozzles,
   wherein each droplet nozzle has an opening at an upper surface of said droplet nozzle member and extends into a lower surface of said droplet nozzle member,
   wherein each droplet nozzle is in communication with said at least one droplet collection groove,
   wherein each droplet nozzle has a heating element for vaporizing a liquid layer of the solution for digital PCR in said droplet nozzle to generate a vapor that moves into a droplet generating oil in said droplet collection groove to generate digital PCR droplets and a generation rate of the digital PCR droplets is controlled by controlling heating time, number of heating, and time intervals of heating of the heating element; and
   wherein a through groove is provided at a bottom of said droplet collection groove, said through groove exposes the plurality of said droplet nozzles, and the through groove and a droplet nozzle hole are located on a same side of the droplet collection groove.

2. The digital PCR system of claim 1, wherein said heating element is arranged on a lower surface or sidewall of said droplet nozzle.

3. The digital PCR system of claim 1, wherein the opening of said droplet nozzle is in a round shape, an ellipse shape, or a polygon shape.

4. The digital PCR system of claim 1, wherein said heating element comprises at least one metal layer.

5. The digital PCR system of claim 1, wherein said PCR system further comprises at least one PCR reagent chamber for storing the solution for digital PCR, said droplet nozzle member has a flow channel, and said plurality of droplet nozzles are in communication with said PCR reagent chamber through said flow channel.

6. The digital PCR system of claim 5, wherein said flow channel comprises at least one main flow channel and a plurality of branch flow channels connected to said main flow channel, and each of said droplet nozzles is connected to one of said plurality of branch flow channels.

7. The digital PCR system of claim 5, wherein said digital PCR system further comprises a substrate, said PCR reagent chamber is arranged in said substrate, and said droplet nozzle member is connected above said substrate.

8. The digital PCR system of claim 7, wherein said substrate comprises a first substrate component and a second substrate component, and said PCR reagent chamber comprises a PCR reagent upper chamber and a PCR reagent lower chamber, said PCR reagent upper chamber has an opening on an upper surface of said first substrate component and through the lower surface of said first substrate component, said PCR reagent lower chamber has an opening on an upper surface of said second substrate component and extends toward and does not reach a lower surface of said second substrate component, and said PCR reagent upper chamber is in communication with and partially overlapped with said PCR reagent lower chamber.

9. The digital PCR system of claim 8, wherein at least one injection hole for the solution for digital PCR is provided on the lower surface of said second substrate component, said digital PCR solution injection hole being connected to said PCR reagent lower chamber.

10. The digital PCR system of claim 9, wherein said PCR reagent lower chamber comprises a first end and a second end, said injection hole for the solution for digital PCR is in communication with said PCR reagent lower chamber at said first end, said PCR reagent lower chamber is in communication with said PCR reagent upper chamber at said second end, said PCR reagent lower chamber being firstly progressively increases in size and then gradually decreases in size in a direction from said first end to said second end.

11. The digital PCR system of claim 10, wherein at least one exhaust port is provided on the lower surface of said second substrate component, said exhaust port is in communication with said PCR reagent upper chamber via a gas passage, said gas passage has an opening on the upper surface of said second substrate component and extends toward and does not reach the lower surface of said second substrate component.

12. The digital PCR system of claim 7, wherein said digital PCR system further comprises a flexible circuit board connected above the upper surface of the substrate, said flexible circuit board has a through hole for accommodating said droplet nozzle member, wherein a plurality of first connection pads and second connection pads are arranged on the surface of said flexible circuit board, and said droplet nozzle member is connected to said first connection pads by conductive wires.

13. The digital PCR system of claim 12, wherein said flexible circuit board is glued to said substrate, a channel being provided on the surface of said substrate for preventing glue from flowing to said droplet nozzle member.

14. The digital PCR system of claim 13, wherein at least two positioning through holes are arranged in said flexible circuit board, and positioning bumps at positions corresponding to the positioning through holes are provided on the surface of said substrate.

15. The digital PCR system of claim 14, wherein said digital PCR system further comprises a controller, said controller comprises a controller housing and a controller circuit board arranged in said controller housing, said controller housing has a support for supporting said substrate, a plurality of conductive pins for circuit connection connected to said circuit connection board of the controller are arranged on a surface of said support, said conductive pins for circuit connection are at positions corresponding to said second connection pads.

16. The digital PCR system of claim 15, wherein at least one position-limiting slot is provided at one end of said substrate, and said controller housing has at least one position-limiting part, wherein said at least one position-limiting slot is configured to receive said at least one position-limiting part so that said controller housing is affixed on said substrate.

17. The digital PCR system of claim 11, wherein a sunken platform for accommodating the first substrate component is provided on a surface of the second substrate component, four corners of the sunken platform have arc-shaped extension spaces, and protrusions around the sunken platform function as a means for positioning when the first substrate component is glued to a sunken platform surface.

18. The digital PCR system of claim 17, wherein an opening area of the digital PCR solution injection hole is larger than an opening area of the exhaust port to support tips of a pipetting gun.

19. The digital PCR system of claim 16, wherein a protuberance is arranged on the back of the droplet generation component to ensure a strong bonding between the droplet generation component and the flexible circuit board.

\* \* \* \* \*